US 6,601,706 B2
United States Patent
McManus et al.

(10) Patent No.: US 6,601,706 B2
(45) Date of Patent: Aug. 5, 2003

(54) PACKAGE FOR ABSORBENT ARTICLES

(75) Inventors: James D. McManus, Appleton, WI (US); Ann M. Nichols, Appleton, WI (US); Paul M. Simons, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/965,930

(22) Filed: Sep. 28, 2001

(65) Prior Publication Data

US 2002/0153271 A1 Oct. 24, 2002

Related U.S. Application Data

(63) Continuation of application No. 09/916,795, filed on Jul. 27, 2001, now abandoned, which is a continuation-in-part of application No. 29/140,508, filed on Apr. 19, 2001.

(51) Int. Cl.[7] .............................................. B65D 85/62
(52) U.S. Cl. ....................................... 206/526; 206/440
(58) Field of Search .......................... 116/205; 206/440, 206/449, 451, 459.5, 471, 494, 812, 526; 229/81, 226, 228, 240, 243, 244; 383/2, 86

(56) References Cited

U.S. PATENT DOCUMENTS

| 900,751 | A | | 10/1908 | Lockwood |
|---|---|---|---|---|
| 1,671,825 | A | | 5/1928 | Johnson |
| 1,750,375 | A | * | 3/1930 | Vinciguera .................. 383/86 |
| 2,573,309 | A | | 10/1951 | Chipkevich |
| 2,603,266 | A | | 7/1952 | Carroll |
| 2,750,033 | A | | 6/1956 | Pickens |
| 3,062,371 | A | | 11/1962 | Patience |
| 3,160,273 | A | | 12/1964 | Reuther et al. |
| 3,314,464 | A | | 4/1967 | Veilleux |
| 3,320,863 | A | | 5/1967 | Ells et al. |
| 3,338,019 | A | | 8/1967 | Trewella et al. |
| 3,405,861 | A | | 10/1968 | Bush |
| 3,420,433 | A | | 1/1969 | Bostwick |
| 3,557,853 | A | | 1/1971 | Jones |
| 3,670,876 | A | | 6/1972 | Davis |

(List continued on next page.)

FOREIGN PATENT DOCUMENTS

| CA | 2025856 | 3/1991 |
|---|---|---|
| CA | 2 109 782 | 5/1995 |
| DE | 83 19 608 | 12/1984 |
| DE | 39 23 839 A1 | 10/1990 |
| EP | 0 419 770 A1 | 4/1991 |
| EP | 1 043 004 A2 | 10/2000 |
| FR | 1 482 194 | 4/1966 |
| WO | WO 94/00362 | 1/1994 |
| WO | WO 98/18682 | 5/1998 |
| WO | WO 98/57610 | 12/1998 |
| WO | WO 99/26576 | 6/1999 |
| WO | WO 02/08087 A2 | 1/2002 |

OTHER PUBLICATIONS

PCT/US01/30964 International Search Report from the European Patent Office dated May 8, 2002.
PCT/US01/44975 International Search Report from the European Patent Office dated May 8, 2002.

*Primary Examiner*—Jim Foster
(74) *Attorney, Agent, or Firm*—Senniger, Powers, Leavitt & Roedel

(57) ABSTRACT

A package including absorbent articles and recloseable packaging. The packaging includes a flexible pocket having a hollow interior for said absorbent articles and an opening extending into the hollow interior for permitting an article to be withdrawn from the hollow interior. The packaging also includes a flap having a proximal end attached to the pocket and a distal end opposite the proximal end. The flap may be moved between an open position to permit an article to be withdrawn through the opening and a closed position to retain the articles in the pocket. The flap has a proximal width at the proximal end and a distal width at the distal end shorter than the proximal width.

24 Claims, 8 Drawing Sheets

U.S. PATENT DOCUMENTS

| | | |
|---|---|---|
| 3,674,195 A | 7/1972 | Stone |
| 3,982,687 A | 9/1976 | Auer et al. |
| 3,990,872 A | 11/1976 | Cullen |
| 4,131,195 A | 12/1978 | Worrell |
| 4,276,982 A | 7/1981 | Sibrava et al. |
| 4,286,639 A | 9/1981 | Murphy |
| 4,441,613 A | 4/1984 | Hain et al. |
| 4,460,088 A | 7/1984 | Rugenstein et al. |
| 4,502,599 A | 3/1985 | Perecman |
| 4,546,029 A | 10/1985 | Cancio et al. |
| 4,550,855 A | 11/1985 | Harrison |
| 4,556,146 A | 12/1985 | Swanson et al. |
| 4,679,693 A | 7/1987 | Forman |
| 4,700,841 A | 10/1987 | Padgett, Jr. et al. |
| 4,713,839 A | 12/1987 | Peppiatt |
| 4,739,879 A | 4/1988 | Nakamura |
| 4,743,245 A | 5/1988 | Lassen et al. |
| 4,838,327 A | 6/1989 | Ambler et al. |
| 4,917,675 A | 4/1990 | Taylor et al. |
| 4,934,535 A | 6/1990 | Muckenfuhs et al. |
| 4,948,028 A | 8/1990 | Vollowitz |
| 4,964,859 A | 10/1990 | Feldman |
| 4,966,286 A | 10/1990 | Muckenfuhs |
| 4,979,613 A | 12/1990 | McLaughlin et al. |
| 5,046,620 A | 9/1991 | Barabino |
| 5,048,687 A | 9/1991 | Suzuki et al. |
| 5,050,742 A * | 9/1991 | Muckenfuhs ............... 206/494 |
| 5,054,619 A * | 10/1991 | Muckenfuhs ............... 206/494 |
| 5,065,868 A | 11/1991 | Cornelissen et al. |
| 5,076,465 A | 12/1991 | Lawson |
| 5,082,112 A | 1/1992 | Dunklee |
| 5,242,057 A | 9/1993 | Cook et al. |
| 5,261,531 A | 11/1993 | Nieves |
| 5,391,136 A | 2/1995 | Makowka |
| 5,413,568 A | 5/1995 | Roach et al. |
| D360,577 S | 7/1995 | Van Loo |
| D365,981 S | 1/1996 | Sullivan |
| 5,560,798 A | 10/1996 | Brusky |
| 5,569,230 A | 10/1996 | Fisher et al. |
| 5,579,916 A | 12/1996 | Manko |
| 5,639,523 A | 6/1997 | Ellis |
| 5,655,842 A | 8/1997 | Hagino |
| 5,730,294 A | 3/1998 | Blosser et al. |
| 5,884,771 A | 3/1999 | McCormick |
| 5,954,201 A | 9/1999 | Finch et al. |
| 5,971,153 A | 10/1999 | Bauer et al. |
| 5,996,797 A | 12/1999 | Flaig |
| 6,039,175 A | 3/2000 | Wright |
| 6,041,928 A | 3/2000 | Jousinen et al. |
| 6,059,100 A | 5/2000 | Jones |
| 6,115,997 A | 9/2000 | Burrow et al. |
| 6,126,009 A | 10/2000 | Shiffler et al. |
| 6,168,022 B1 | 1/2001 | Ward et al. |
| 6,257,473 B1 | 7/2001 | Ringelstetter |
| 6,338,572 B1 | 1/2002 | Schneck |

* cited by examiner

PACKAGE FOR ABSORBENT ARTICLES

CROSS-REFERENCE TO RELATED APPLICATION

This is a continuation of U.S. patent application Ser. No. 09/916,795, filed Jul. 27, 2001, entitled, "PACKAGE FOR ABSORBENT ARTICLES", abandoned, which is a continuation-in-part of U.S. patent application Ser. No. 29/140,508, filed Apr. 19, 2001, entitled, "PACKAGE FOR ABSORBENT ARTICLES", pending, both of which are hereby incorporated by reference in their respective entireties.

BACKGROUND OF THE INVENTION

The present invention relates generally to a package, and more particularly to a package for absorbent articles.

Absorbent articles such as panty liners, feminine napkins and tampons are frequently carried about in purses, backpacks and briefcases until needed. Typically, the articles are put in these containers loose. Unfortunately, these containers do not always provide a hygienic environment for the articles, and thus the articles can become dirty and/or damaged. Further, the articles can become scattered about in the containers so they are difficult to find when needed.

In the past, specifically designed pouches have been distributed for holding several absorbent articles at a time. These pouches reduce contact between the articles and potentially non-hygienic environments, and make the articles easier to find when needed. The pouches are made from durable materials such as heavy vinyl so they can be reused, but reuse necessitates the pouches be refilled from time to time. Further, the pouches frequently become non-hygienic after extended use, requiring them to be cleaned or discarded and replaced.

To avoid these problems, some persons use clear plastic sandwich bags to hold the articles. These bags usually maintain a hygienic environment for the articles and make the articles easier to find when needed. Although the bags must be filled from time to time, they are readily disposable and replaceable thereby reducing some of the concerns and inconveniences caused by extended use. However, because the bags are transparent, they permit the contents of the bags to be viewed. Some users desire more discreet packaging. Thus, there is a need for a discreet, disposable and economical reclosable package for holding several articles at a time.

One type of packaging which meets the previously mentioned need is described in co-assigned U.S. patent application Ser. No. 09/713,496, entitled "Package", filed Nov. 15, 2000, which is hereby incorporated by reference in its entirety. As shown in FIG. 1, this packaging (generally designated by the reference number 10) includes a pocket 12 for holding the articles and an opening (not shown) for withdrawing articles from the pocket when needed. Further, the package 10 includes a rectangular flap 14 for selectively covering the opening. The flap 14 has an adhesive closure (not shown) for holding the flap against the pocket 12 when covering the opening. It has been noted that if the flap 14 is not aligned with the pocket 12 when closed as illustrated in FIG. 2, a side edge 16 and a corner 18 of the flap extends past the pocket presenting an unattractive appearance. Thus, there is a need for a package 10 which permits misalignment between the flap 14 and the pocket 12 without exposing an edge 16 or corner 18 of the flap.

SUMMARY OF THE INVENTION

Briefly, apparatus of this invention is a package comprising a plurality of absorbent articles and reclosable packaging. The packaging includes a flexible pocket having a hollow interior sized and shaped for receiving the plurality of absorbent articles and an opening extending into the hollow interior of the pocket sized and shaped for permitting at least one of the plurality of articles to be withdrawn from the hollow interior of the pocket through the opening. Further, the packaging includes a flap having a proximal end attached to the pocket and a distal end opposite the proximal end. The flap is adapted for covering the opening to retain the plurality of absorbent articles in the hollow interior of the pocket. The flap is selectably moveable between an open position in which the opening is generally unobstructed by the flap to permit the at least one article to be withdrawn through the opening and a closed position in which the flap covers the opening and an exterior area of the pocket to retain the plurality of articles in the pocket and to prevent the at least one article from passing through the opening. The flap has a proximal width at the proximal end and a distal width at the distal end shorter than the proximal width.

In another aspect, the present invention includes a package comprising a plurality of absorbent articles and reclosable packaging including a flexible pocket, an opening, and a flap. The flap may be rotated when in the closed position about an axis extending normal to a surface of the flap by as much as about twenty degrees without extending past a side of the pocket.

In still another aspect, the present invention includes a package comprising a plurality of absorbent articles and reclosable packaging including a flexible pocket and an opening. Further, the packaging includes a flexible hinge attached to the pocket adjacent the opening. The hinge has a width substantially equal to a width of the opening and a length equal to between about 0.05 times and about 0.20 times a combined uncompressed thickness of the plurality of absorbent articles. In addition, the packaging includes a flap attached to the hinge adapted for covering the opening to retain the plurality of absorbent articles in the hollow interior of the pocket.

Other features of the present invention will be in part apparent and in part pointed out hereinafter.

BRIEF DESCRIPTION OF THE DRAWINGS

Corresponding reference characters indicate corresponding parts throughout the several views of the drawings.

DETAILED DESCRIPTION OF THE PREFERRED EMBODIMENTS

Figure 1:
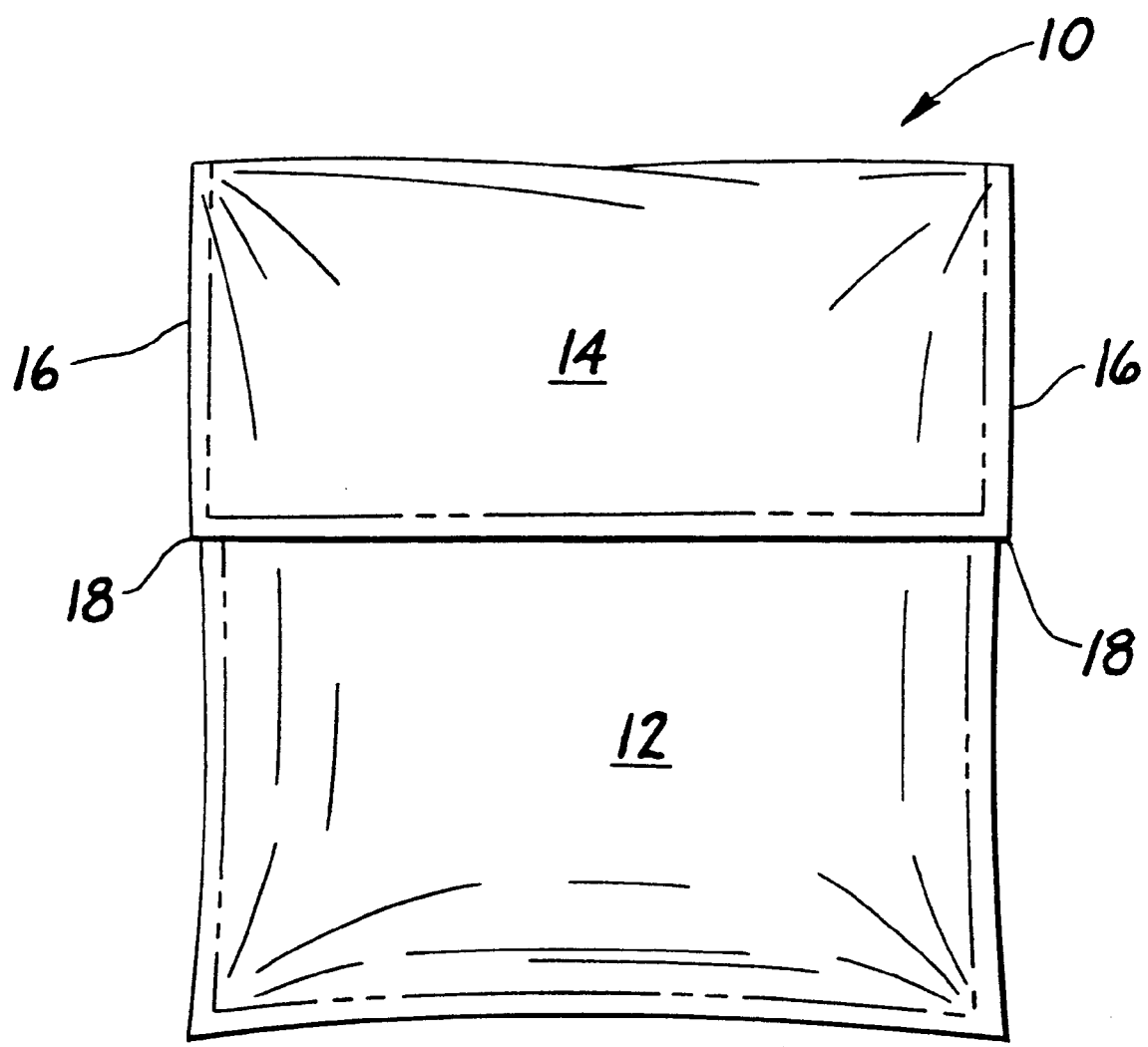
FIG. 1 is a front elevation of a package for holding panty liners.
Figure 2:
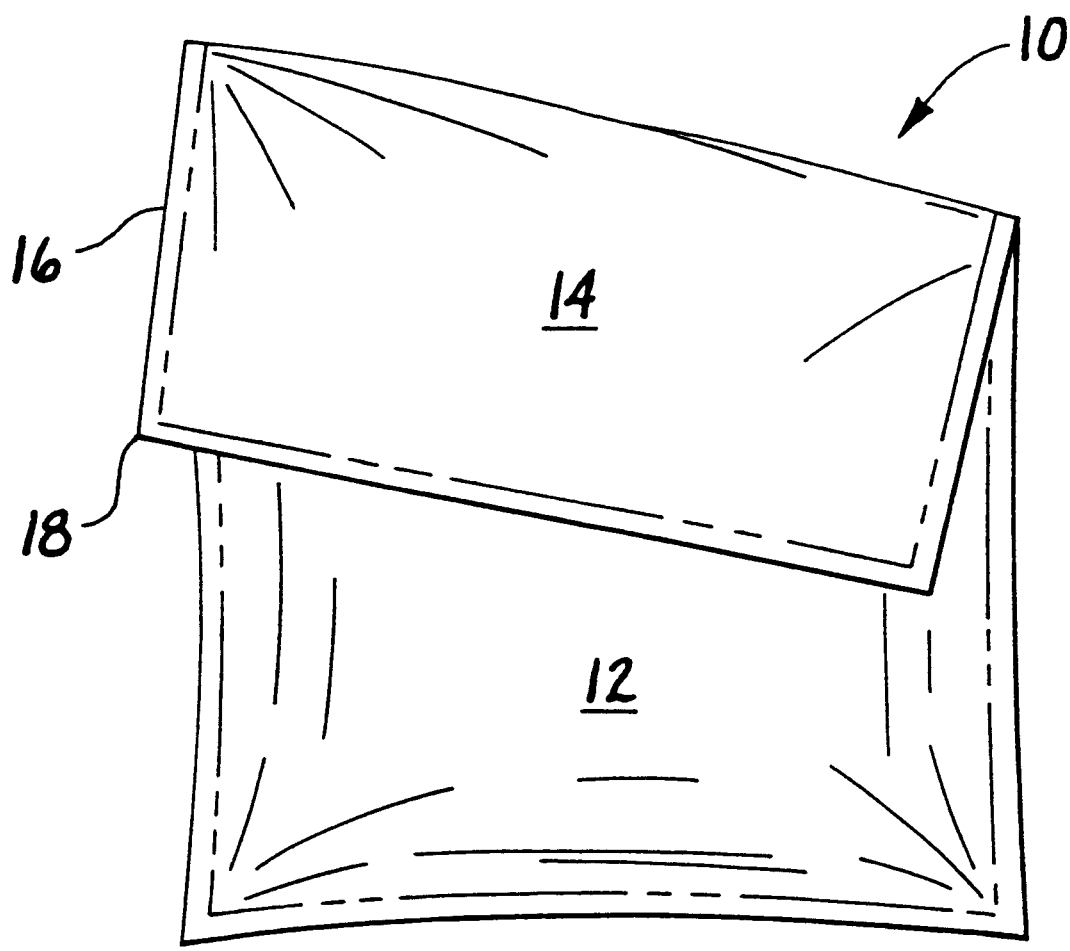
FIG. 2 is a front elevation of the package showing a flap misaligned with a pocket of the package.
Figure 3:
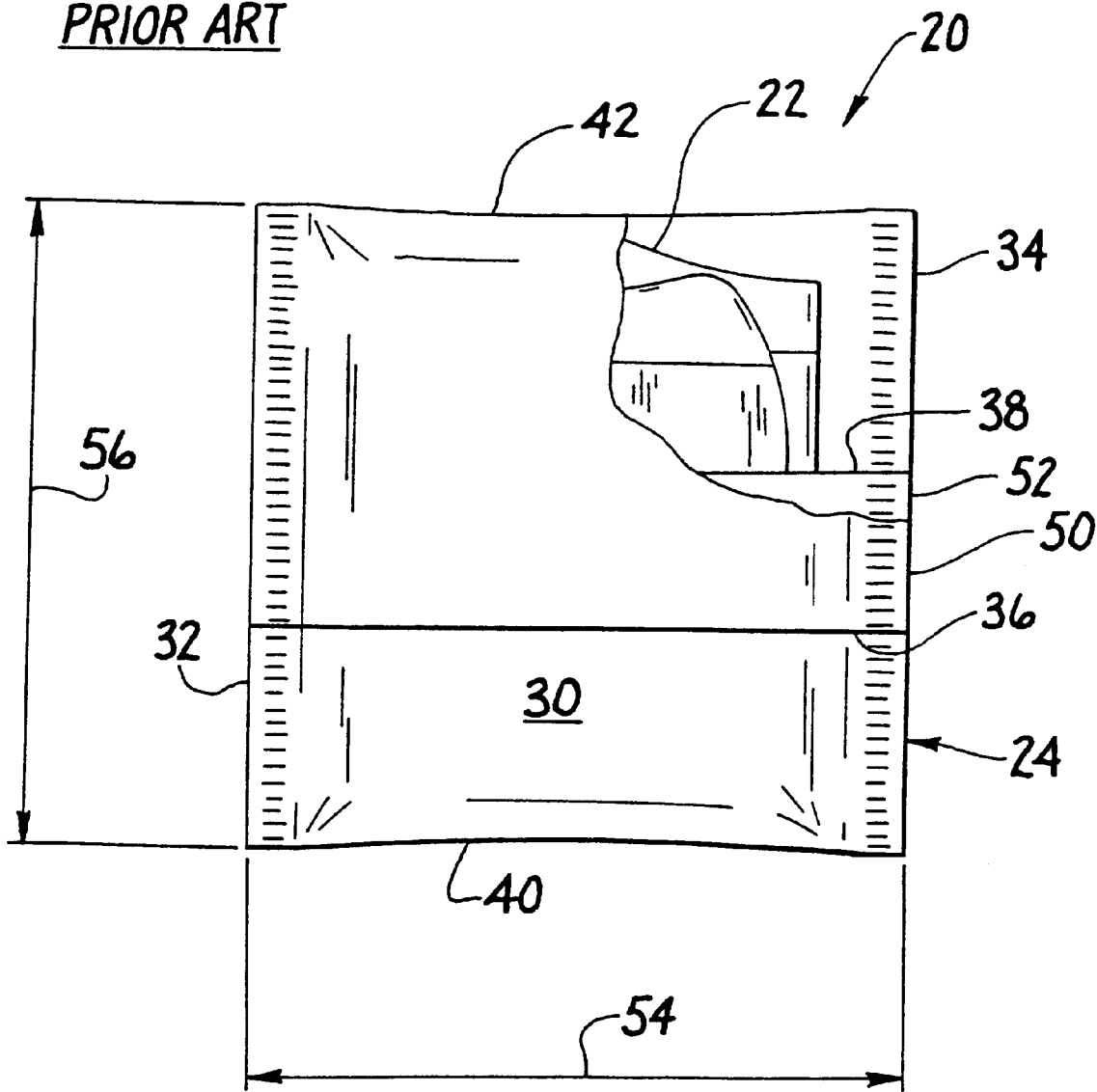
FIG. 3 is a front elevation of a prior art panty liner surrounded by a removable wrapper in partial section.

Referring now to the drawings and in particular to FIG. 3, a conventional individually wrapped absorbent article is designated in its entirety by the reference numeral 20. Although the absorbent article 20 shown in FIG. 3 is a panty liner 22 surrounded by a wrapper, generally designated by 24, those skilled in the art will appreciate that the present invention may be applied to other absorbent articles 20 such as feminine napkins, tampons, interlabial pads, other feminine care products, adult care products, child care products and infant care products. Further, those skilled in the art will appreciate that although the illustrated articles 20 are individually wrapped, the articles may be unwrapped without departing from the scope of the present invention.

The panty liner 22 shown in FIG. 3 is folded twice in a conventional manner to present a generally flat and generally rectangular article. Although the folded panty liner 22 may have other sizes without departing from the scope of the present invention, in one embodiment the folded liner has a width of about 50 millimeters, a length of about 70 millimeters and a thickness of about 5 millimeters. It is also envisioned that the panty liner 22 may be unfolded and/or non-rectangular without departing from the scope of the present invention.

Although the wrapper 24 may be made in other ways without departing from the scope of the present invention, in one embodiment the wrapper includes a rectangular sheet 30 having opposite side edges 32, 34 and opposite end edges 36, 38. A first fold 40 in the sheet 30 extending between the side edges 32, 34 forms a bottom of the wrapper 24, and a second fold 42 in the sheet extending between the side edges generally parallel to and above the first fold forms a top of the wrapper. A margin 50 of the sheet 30 adjacent the end edge 36 overlaps a margin 52 of the sheet adjacent the end edge 38. It is envisioned that it may be desirable to join the corresponding side edges 32, 34 to themselves. Although the side edges 32, 34 of the rectangular sheet 30 may be joined in other ways (such as with adhesives or by heat sealing) without departing from the scope of the present invention, in one embodiment the side edge margins are joined by conventional mechanical fastening means as shown.

Although the wrapped article 20 may have other sizes without departing from the scope of the present invention, in one embodiment the article has a width 54 of about 75 millimeters, a length 56 of about 75 millimeters and a thickness 58 (FIG. 6) of about 5 millimeters. Further, although the dimensions of the article 20 may vary from article to article without departing from the scope of the present invention, in one embodiment the dimensions are generally uniform. In addition, the dimensions may vary within a given article or they may be invariant without departing from the scope of the present invention. Although the wrapper 24 may be made of other materials without departing from the scope of the present invention, in one embodiment the wrapper is made from low density polyethylene sheet material having a thickness of about 38 microns. It is further envisioned that the wrapper 24 may have an adhesive or other closure (not shown) without departing from the scope of the present invention.

Figure 4:
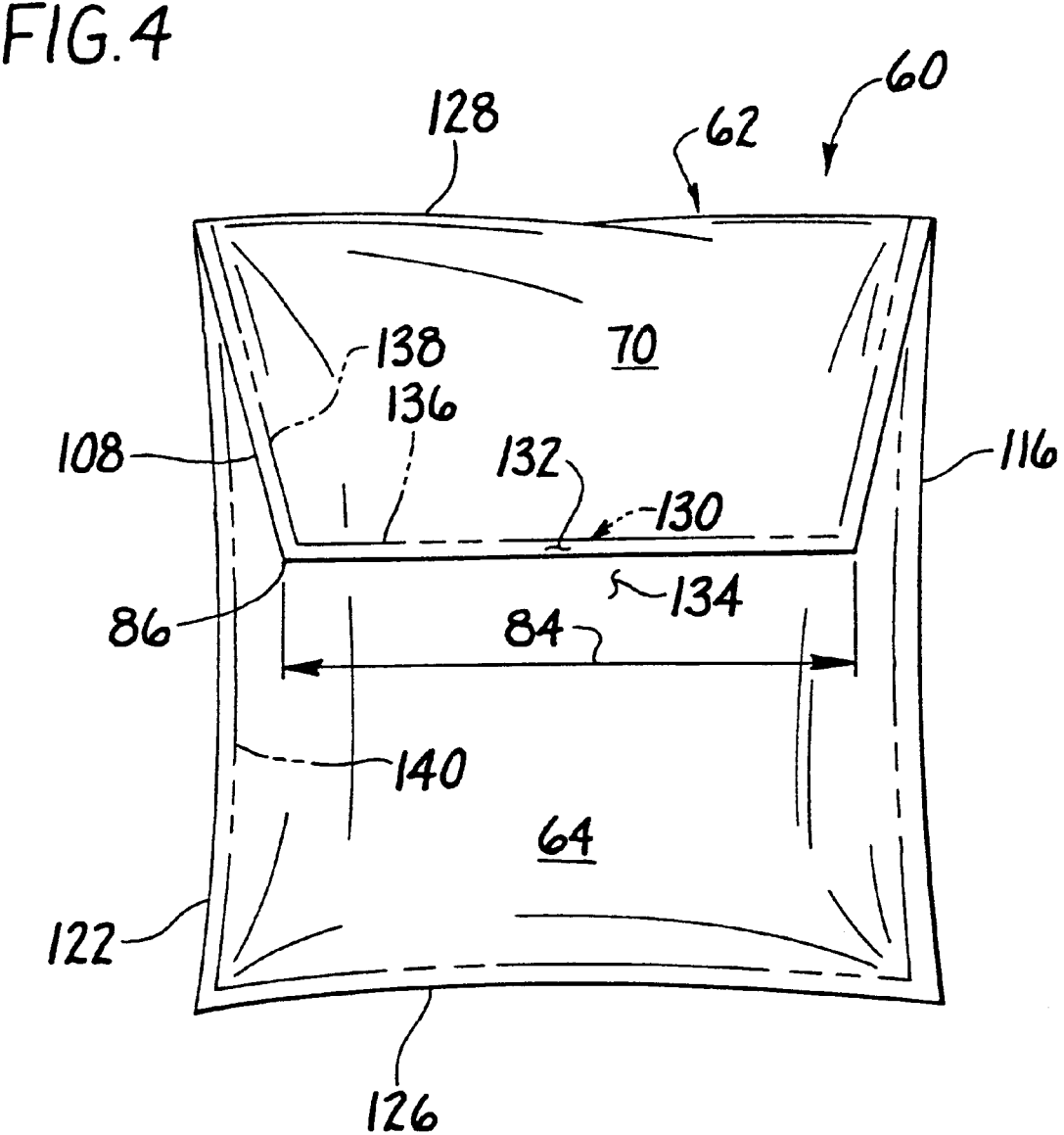
FIG. 4 is a front elevation of a package of the present invention showing a flap of the package in a closed position.
Figure 5:
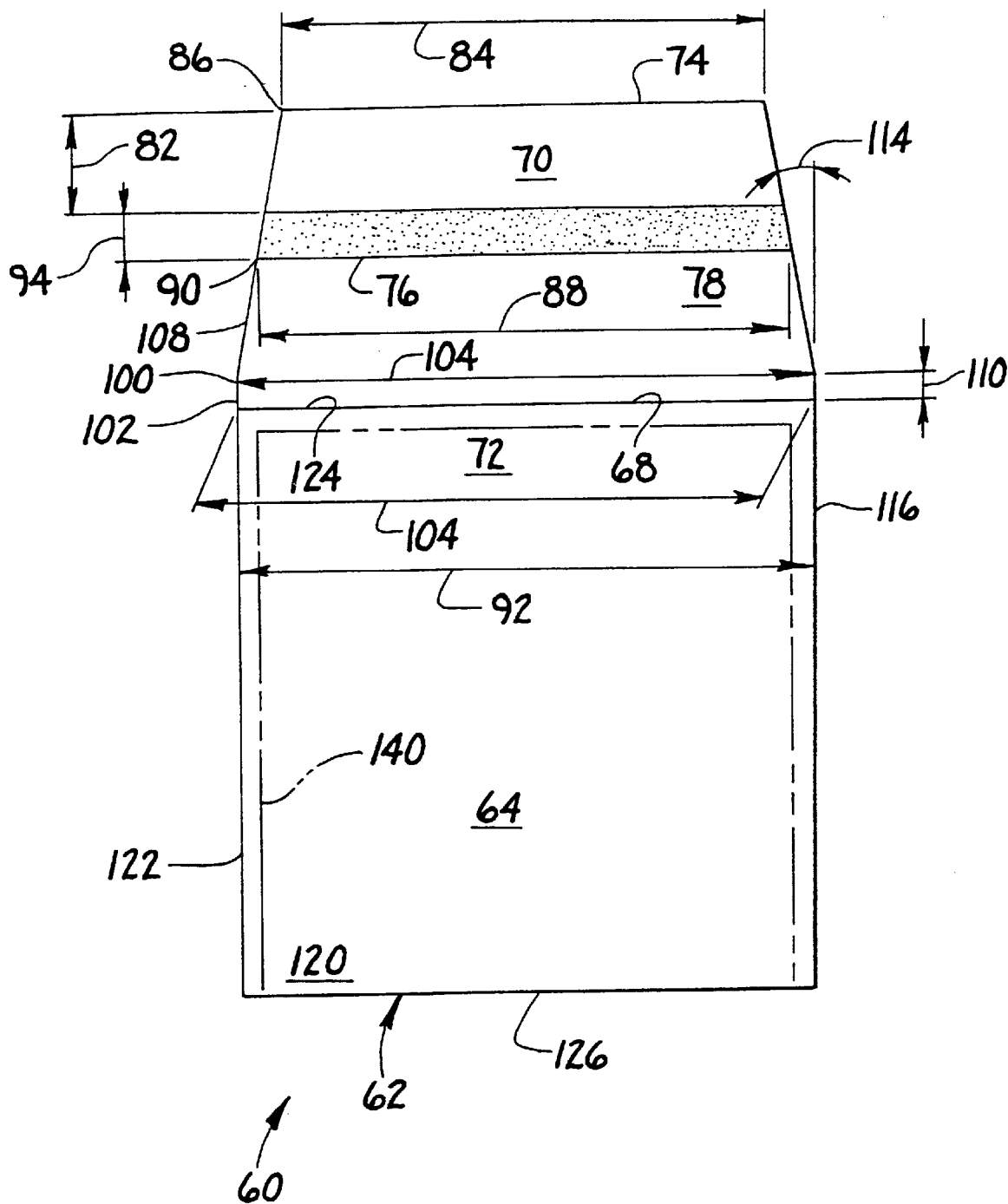
FIG. 5 is a front elevation of the package showing the flap in an open position.
Figure 6:
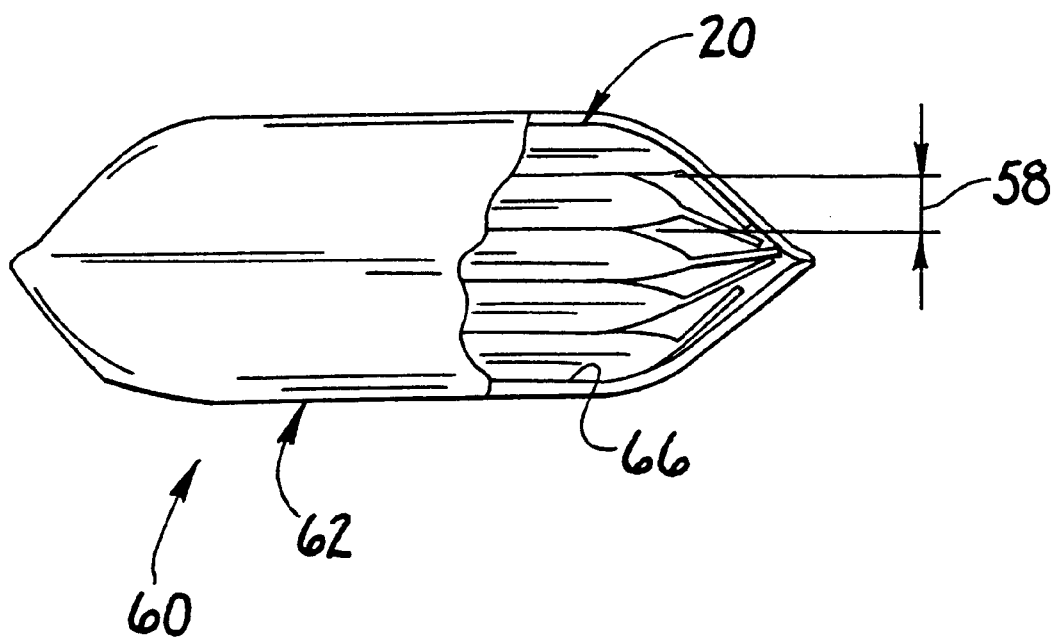
FIG. 6 is a top plan of the package in partial section.

As illustrated in FIGS. 4–6, a utility package of the present invention is designated in its entirety by the reference number 60. The package 60 generally comprises a plurality of absorbent articles 20 (FIG. 3) and reclosable packaging, generally designated by 62. As previously mentioned, it is envisioned that the articles 20 may be folded or unfolded and individually wrapped or unwrapped without departing from the scope of the present invention. Although the articles 20 may be arranged in other ways without departing from the scope of the present invention, in one embodiment the articles are arranged in face-to-face relation in a stack as illustrated in FIG. 6. The package 60 includes a number of articles 20 which is selected for the convenience of an end user. For example, the package 60 may include less than about eight absorbent articles 20 to provide a supply of articles for about one week or less. It is envisioned that it may be desirable that the package 60 include about five absorbent articles 20 to provide a supply of articles for one conventional work week (i.e., five days).

The packaging 62 includes a flexible pocket 64 having a hollow interior 66 sized and shaped for receiving the preselected number of absorbent articles 20 as shown in FIG. 6. An opening 68 (FIG. 5) extends into the hollow interior 66 of the pocket 64. The opening 68 is sized and shaped for permitting at least one of the plurality of articles 20 to be withdrawn from the hollow interior 66 of the pocket 64. Further, the packaging 62 includes a flap 70 attached to the pocket 64 adapted for covering the opening 68 to retain the plurality of articles 20 in the hollow interior 66 of the pocket 64. The flap 70 is selectably moveable between an open position as illustrated in FIG. 5 in which the opening 68 is generally unobstructed by the flap to permit at least one article 20 to be withdrawn through the opening and a closed position as shown in FIG. 4 in which the flap covers the opening and an exterior area 72 (FIG. 5) of the pocket 64 to retain the articles in the pocket and to prevent the articles from passing through the opening. In one embodiment, the flap 70 is trapezoidal and has a substantially straight distal end 74, but those skilled in the art will appreciate that the flap 70 may have other shapes such as semi-circular or triangular without departing from the scope of the present invention.

As illustrated in FIG. 5, a closure 76 is positioned on an inner face or interior surface 78 of the flap 70 for releasably holding the flap in the closed position. It is envisioned that the closure 76 may be positioned on the exterior area 72 of the pocket 64 instead of or in addition to being positioned on the flap 70. Preferably, the closure 76 permits the flap 70 to be positioned in a different location on the pocket 64 during successive closings when successive articles 20 are removed from the interior 66 of the pocket to permit the packaging 62 to conform to the remaining articles in the interior of the pocket. Although other closures 76 may be used without departing from the scope of the present invention, in one embodiment the closure is an adhesive material such as a conventional resealable hot melt adhesive or a resealable two sided tape for releasably holding the flap 70 in the closed position.

Although the closure 76 may be positioned at other locations without departing from the scope of the present invention, in one embodiment the closure is spaced from the distal end 74 of the flap 70 to permit a free portion of the flap to be grasped and separated from the pocket 64 to grip the flap for releasing the closure. It is envisioned that it may be desirable that the closure 76 be spaced from the distal end 74 of the flap 70 by a distance 82 of at least about 4 millimeters. It is further envisioned that it may be desirable that the distance 82 be about 16 millimeters.

Although the closure 76 may have other shapes without departing from the scope of the present invention, in one embodiment the closure is an elongate strip of adhesive material extending substantially parallel to the distal end 74 of the flap 70. In one embodiment, the strip of adhesive material is substantially continuous and uninterrupted along its entire length, but it is envisioned that other embodiments may have adhesive material which is discontinuous and/or interrupted along its length without departing from the scope of the present invention. In addition, it is envisioned that it may be desirable that the strip extend over a distance greater than or equal to a distal width 84 of the flap 70 so the corners 86 of the flap are held in place near the pocket 64. Further, it is envisioned that it may be desirable that the strip extend over an entire width of the flap 70 corresponding to the strip. As shown in FIG. 5, the closure 76 preferably has an overall length 88 extending between opposite lateral ends 90 of the closure which is less than a corresponding width 92 of the pocket 64. Although the elongate strip may have other widths without departing from the scope of the present invention, in one embodiment the strip has a width 94 of less than about 20 millimeters and more than about 2 millimeters. It may be desirable that the width 94 of the strip be about 7 millimeters.

The flap 70 has a proximal end 100 attached to the pocket 64 by an integrally formed flexible hinge 102 attached to the pocket adjacent the opening 68. The flap has a proximal width 104 at the proximal end 100 substantially equal to a width 106 of the opening. The previously mentioned distal width 84 at the distal end 74 of the flap 70 is shorter than the proximal width 104. The flap 70 is tapered between the proximal end 100 and the distal end 74 so it has converging opposite side edges 108. Although these side edges 108 may have other shapes and configurations without departing from the scope of the present invention, in one embodiment the side edges are substantially straight.

Figure 7:
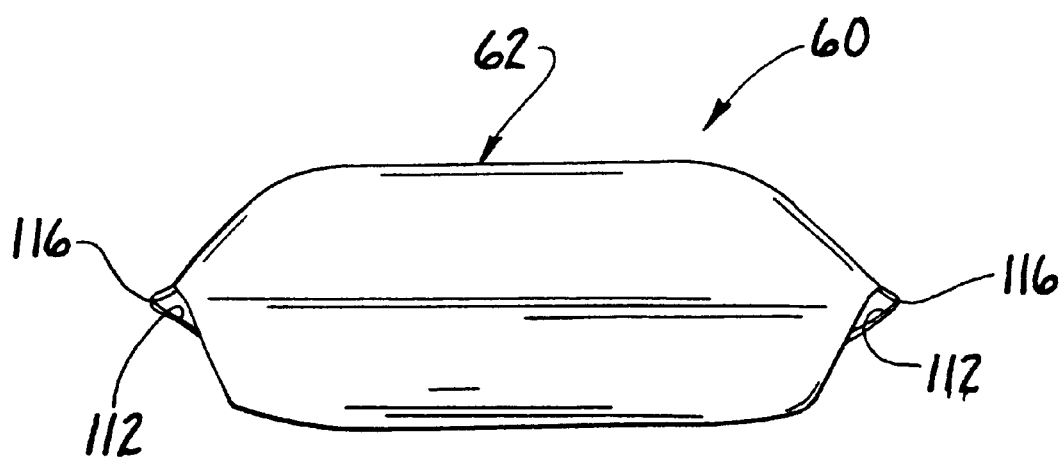
FIG. 7 is a top plan of a package showing a corner hole flaw which is overcome by one aspect of the present invention.

As further illustrated in FIG. 5, the converging side edges 108 define a tapered portion of the flap 70 spaced from the opening 68 by a distance 110. Although the tapered portion of the flap 70 may be spaced from the opening 68 by other distances without departing from the scope of the present invention, in one embodiment the tapered portion of the flap is spaced from the opening by a distance 110 of between about 1.5 millimeters and about 4.5 millimeters. Further, it may be preferable for the tapered portion of the flap 70 to be spaced from the opening 68 by a distance 110 equal to between about 0.05 times and about 0.20 times a combined uncompressed thickness of the absorbent articles 20. For example, if the package 60 includes five absorbent articles 20, each having a thickness of about five millimeters, the combined uncompressed thickness of the articles would be about 25 millimeters, and the tapered portion of the flap 70 would be spaced from the opening 68 by a distance 110 of between about 1.25 millimeters and about 5 millimeters. It is further envisioned that it may be preferable for the tapered portion to be spaced from the opening 68 by a distance 110 equal to between about 0.058 times and about 0.173 times the combined uncompressed thickness of the absorbent articles 20. As will be appreciated by those skilled in the art, spacing the proximal end 100 from the opening 68 and including the hinge 102 having a length equal to the width 104 of the opening prevents holes 112 (FIG. 7) from forming at the ends of the hinge when the flap 70 is in the closed position. Thus, the hinge 102 and flap 70 cover the entire opening 68 so debris is less likely to enter the interior 66 of the pocket 64 when the flap is in the closed position. In addition, because the hinge 102 is not longer than the width 104 of the opening 68, it does not overhang the pocket 64 when the flap is in the closed position. As will be further appreciated by those skilled in the art, the distance 110 by which the tapered portion is spaced from the opening 68 corresponds to the length of the hinge 102 and the width of the proximal end 100 of the flap 70 corresponds to the width of the hinge.

Figure 8:
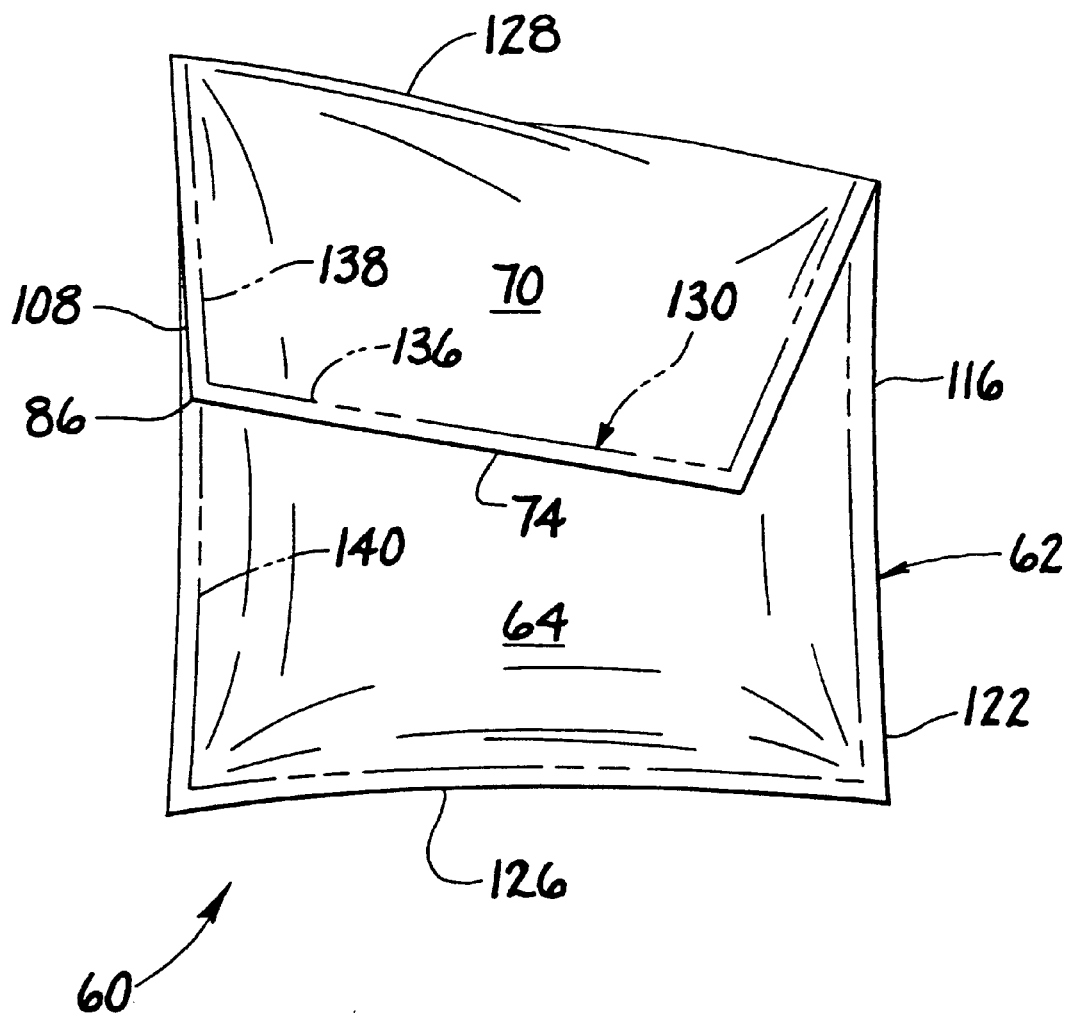
FIG. 8 is a front elevation of the package showing the flap misaligned with the pocket in the closed position.

Although the straight side edges 108 of the flap 70 may extend at other angles without depart from the scope of the present invention, in one embodiment each side edge extends at an angle 114 of between about ten degrees and about twenty degrees with respect to corresponding sides 116 of the pocket when the distal end 74 of the flap 70 is substantially perpendicular to the sides of the pocket. As will be appreciated by those skilled in the art, this configuration allows the flap 70 to be rotated when in the closed position about an axis extending normal to the surface 78 of the flap as illustrated in FIG. 8 by as much as about twenty degrees without either the side edges 108 or the corners 86 extending past the sides 116 of the pocket 64.

Although the packaging 62 may be made in other ways without departing from the scope of the present invention, in one embodiment illustrated in FIG. 5 the packaging comprises a sheet 120 having opposite side edges 122 and opposite end edges 74, 124. A first fold 126 extending between the side edges 122 forms a bottom of the packaging 62, and a second fold 128 (FIG. 4) extending between the side edges generally parallel to and above the first fold forms a top of the packaging. Portions of the side edges 122 are joined to form opposite sides 116 of the pocket 64. Although the side edges 122 may be joined in other ways (such as with adhesives or by mechanical fastening) without departing from the scope of the present invention, in one embodiment they are joined by conventional heat sealing. Although the packaging 62 may be made from other materials without departing from the scope of the present invention, in one embodiment the packaging is made from a heat sealable polymer sheet material such as a material containing about 80 percent polyethylene and about 20 percent other polyolefins having a thickness of between about 0.001 inches and about 0.002 inches available from Shanghai Zihua Enterprise Company, Limited of Shanghai, China. It is further envisioned that the packaging 62 may be made from coated paper, woven material, non-woven material, polyethylene, polypropylene, co-polymers, extruded polymer, thermoformed materials, and/or cardboard without departing from the scope of the present invention. Although in one embodiment the pocket 64 is substantially free of gussets, in an alternate embodiment the sides of the pocket may include conventional gussets (not shown) to provide the packaging 62 with a substantially flat bottom. Although other sequences are envisioned as being within the scope of the present invention, in one embodiment the sheet 120 is printed, the first fold 126 is made and the side edges 122 are heat sealed to form the pocket 64. Once the pocket 64 is formed, the closure 76 is applied to the inner face 78 of the flap 70, the side edges 108 of the flap 70 are cut to their final shape and the packaging 62 filled with the plurality of absorbent articles 20. Once the packaging 62 is filled, the second fold 128 is made and the closure 76 is sealed to complete the package 60.

As illustrated in FIG. 4, it may be desirable that the flap 70 and/or the pocket 64 include a visual indicator, generally designated by 130, for distinguishing the edge 74 of the flap from the pocket. The indicator 130 improves visual identification of the edge 74 of the flap 70 when grasping the flap to move it toward its open position. The visual indicator 130 comprises visually contrasting surface treatments on the flap 70 and the pocket 64. Although other visually contrasting surface treatments may be used without departing from the scope of the present invention, in one embodiment the visually contrasting surface treatments include a first color on at least a portion of an exterior surface or outer face 132 of the flap 70 and a second color on at least a portion of an exterior surface 134 of the pocket 64. Further, it may be desirable that one of the colors be a raw material color of the packaging material and the other color be printed on the packaging 62. For example, if the raw material color of the packaging 62 is white, a lower edge margin 136 and opposite side margins 138 of the flap 70 may be substantially free of printing, and a central portion of the flap may include printing of a contrasting color (e.g., blue). The margins 136, 138 are delineated by phantom lines in the drawings. In addition to omitting printing from the edge margins 136, 138 of the flap 70, it may be desirable that the side margins 140 of the pocket 64 (delineated by phantom lines) be substantially free of printing, to prevent printing discoloration when the sides are heat sealed.

In view of the above, it will be seen that the several objects of the invention are achieved and other advantageous results attained.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. A package comprising a plurality of absorbent articles, each having a width, and reclosable packaging including:
    a flexible pocket having a hollow interior sized and shared for receiving said plurality of absorbent articles;
    an opening extending into the hollow interior of the pocket sized and shared for permitting at least one of said plurality of to be withdrawn from the hollow interior of the pocket through the opening, the opening having a width at least equal to the width of one of said absorbent articles; and
    a flap having a flexible hinge at a proximal end attached to the pocket adjacent the opening, said flap having a distal end opposite the proximal end, said flap being selectably moveable between an open position in which the opening is generally unobstructed by said flap to permit said at least one article to be withdrawn through the opening and a closed position in which the flap covers the opening and an exterior area of the pocket to retain said plurality of articles in the pocket and to prevent said at least one article from passing through the opening, the flap and pocket substantially enclosing and covering the absorbent articles in the closed position of the flap, wherein said flap has a proximal width at said proximal end and a distal width at said distal end shorter than said proximal width thereby defining a tapered portion between the proximal end and the distal end and wherein said hinge has a width substantially equal to a width of the opening and a length sized to substantially cover said opening such that said tapered portion is spaced from said opening by said flexible hinge, wherein the tapered portion is spaced from the opening by a distance of between about 1.5 millimeters and about 4.5 millimeters.

2. A package as set forth in claim 1 wherein said proximal width of the flap is substantially equal to a width of the opening.

3. A package as set forth in claim 1 wherein said tapered portion has opposite side edges and at least a portion of each side edge is substantially straight.

4. A package as set forth in claim 1 wherein the tapered portion is spaced from the opening by a distance equal to between about 0.052 times and about 0.173 times a combined uncompressed thickness of said plurality of absorbent articles.

5. A package as set forth in claim 3 wherein said tapered portion is trapezoidal.

6. A package as set forth in claim 3 wherein the straight portion of each side edge extends at an angle of between about ten degrees and about twenty degrees with respect to corresponding sides of the pocket when the distal end of the flap is substantially perpendicular to the sides of the pocket.

7. A package as set forth in claim 1 wherein the flip may be rotated when in the closed position about an axis extending normal to a surface of the flap by as much as about twenty degrees without extending past a side of the pocket.

8. A package as set forth in claim 1 wherein said hinge has a width substantially equal to a width of the opening and a length equal to between about 0.05 times and about 0.20 times a combined uncompressed thickness of said plurality of absorbent articles.

9. A package comprising a plurality of absorbent articles, each having a width, and reclosable packaging including:
    a flexible pocket having a hollow interior sized and shaped for receiving said plurality of absorbent articles;
    an opening extending into the hollow interior of the pocket sized and shaped for permitting at least one of said plurality of articles to be withdrawn from the hollow interior of the pocket through the opening, the opening having a width at least equal to the width of one of said absorbent articles; and
    a flap comprising a flexible hinge attached to the pocket adapted for covering the opening to retain said plurality of absorbent articles in the hollow interior of the pocket, said flap being selectably moveable between an open position in which the opening is generally unobstructed by said flap to emit said at least one article to be withdrawn through the opening and a closed position in which the flap covers the opening and an exterior area of the pocket to retain said plurality of articles in the pocket and to prevent said at least one article from passing through the opening, the flap and pocket substantially enclosing and covering the absorbent articles in the closed position of the flap, wherein the flap may be rotated when in the closed position about an axis extending normal to a surface of the flag by as much as about twenty degrees without extending past a side of the pocket, wherein said flexible hinge defines a proximal end of said flap, said flap having a distal end opposite the proximal end, and a tapered portion between the proximal end and the distal end, and wherein said hinge is sized to substantially cover said opening such that said tapered portion is spaced from said opening by said flexible hinge, wherein the tapered portion is spaced from the opening by a distance of between about 1.5 millimeters and about 4.5 millimeters.

10. A package as set forth in claim 9 wherein said tapered portion has opposite side edges and at least a portion of each side edge is substantially straight.

11. A package as set forth in claim 9 wherein the tapered portion is spaced from the opening by a distance equal to between about 0.05 times and about 0.20 times a combined uncompressed thickness of said plurality of absorbent articles.

12. A package as set forth in claim 9 wherein said tapered portion is trapezoidal.

13. A package as set forth in claim 9 wherein said hinge has a width substantially equal to a width of the opening and a length equal to between about 0.05 times and about 0.20 times a combined uncompressed thickness of said plurality of absorbent articles.

14. A package comprising a plurality of absorbent articles and recloseable packaging including:
   a flexible pocket having a hollow interior sized and shaped for receiving said plurality of absorbent articles;
   an opening extending into the hollow interior of the pocket sized and shaped for permitting at least one of said plurality of articles to be withdrawn from the hollow interior of the pocket through the opening;
   a flexible hinge attached to the pocket adjacent the opening, said hinge having a width substantially equal to a width of the opening and a length equal to between about 0.05 times and about 0.20 times a combined uncompressed thickness of said plurality of absorbent articles; and
   a flap attached to the hinge adapted for covering the opening to retain said plurality of absorbent articles in the hollow interior of the pocket, said flap being selectably moveable between an open position in which the opening is generally unobstructed by said flap to permit said at least one article to be withdrawn through the opening and a closed position in which the flap covers the opening and an exterior area of the pocket to retain said plurality of articles in the pocket and to prevent said at least one article from passing through the opening.

15. A package as set forth in claim 14 wherein the hinge has a length equal to between about 0.058 times and about 0.173 times a combined uncompressed thickness of said plurality of absorbent articles.

16. A package as set forth in claim 14 wherein said flap includes a proximal end attached to the hinge, a distal end opposite the proximal end, and said flap includes a tapered portion between the proximal end and the distal end.

17. A package as set forth in claim 16 wherein said tapered portion has opposite side edges and at least a portion of each side edge is substantially straight.

18. A package as set forth in claim 17 wherein said tapered portion is trapezoidal.

19. A package as set forth in claim 17 wherein the straight portion of each side edge extends at an angle of between about ten degrees and about twenty degrees with respect to corresponding sides of the pocket when the distal end of the flap is substantially parallel to the proximal end of the flap.

20. A package comprising a plurality of absorbent articles and reclosable packaging including:
   a flexible pocket having a hollow interior sized and shaped for receiving said plurality of absorbent articles;
   an opening extending into the hollow interior of the pocket sized and shaped for permitting at least one of said plurality of articles to be withdrawn from the hollow interior of the pocket through the opening; and
   a flap having a proximal end attached to the pocket and a distal end opposite the proximal end, said flap being adapted for covering the opening to retain said plurality of absorbent articles in the hollow interior of the pocket, said flap being selectably moveable between an open position in which the opening is generally unobstructed by said flap to permit said at least one article to be withdrawn through the opening and a closed position in which the flap covers the opening and an exterior area of the pocket to retain said plurality of articles in the pocket and to prevent said at least one article from passing through the opening, wherein said flap has a proximal width at said proximal end and a distal width at said distal end shorter than said proximal width;
   the flap further including a tapered portion between the proximal end and the distal end, said tapered portion having opposite side edges and at least a portion of each side edge is substantially straight, said tapered portion being spaced from the opening by a distance equal to between about 0.05 times and about 0.20 times a combined uncompressed thickness of said plurality of absorbent articles.

21. A package as set forth in claim 20 wherein said tapered portion is spaced from the opening by a distance equal to between about 0.058 times and about 0.173 times a combined uncompressed thickness of said plurality of absorbent articles.

22. A package comprising a plurality of absorbent articles and reclosable packaging including:
   a flexible pocket having a hollow interior sized and shaped for receiving said plurality of absorbent articles;
   an opening extending into the hollow interior of the pocket sized and shaped for permitting at least one of said plurality of articles to be withdrawn from the hollow interior of the pocket through the opening; and
   a flap having a proximal end attached to the pocket and a distal end opposite the proximal end, said flap being adapted for covering the opening to retain said plurality of absorbent articles in the hollow interior of the pocket, said flap being selectably moveable between an open position in which the opening is generally unobstructed by said flap to permit said at least one article to be withdrawn through the opening and a closed position in which the flap covers the opening and an exterior area of the pocket to retain said plurality of articles in the pocket and to prevent said at least one article from passing through the opening, wherein said flap has a proximal width at said proximal end and a distal width at said distal end shorter than said proximal width;
   a flexible hinge attached to the pocket adjacent the opening, said flap being attached to the hinge, said hinge having a width substantially equal to a width of the opening and a length equal to between about 0.05 times and about 0.20 times a combined uncompressed thickness of said plurality of absorbent articles.

23. A package comprising a plurality of absorbent articles and reclosable packaging including:
   a flexible pocket having a hollow interior sized and shaped for receiving said plurality of absorbent articles;
   an opening extending into the hollow interior of the pocket sized and shaped for permitting at least one of said plurality of articles to be withdrawn from the hollow interior of the pocket through the opening; and
   a flap attached to the pocket adapted for covering the opening to retain said plurality of absorbent articles in the hollow interior of the pocket, said flap being selectably moveable between an open position in which the opening is generally unobstructed by said flap to permit said at least one article to be withdrawn through the opening and a closed position in which the flap covers the opening and an exterior area of the pocket to retain said plurality of articles in the pocket and to prevent said at least one article from passing through the opening, wherein the flap may be rotated when in the closed position about an axis extending normal to a surface of the flap by as much as about twenty degrees without extending past a side of the pocket;

the flap further including a tapered portion having opposite side edges, at least a portion of each side edge being substantially straight, the tapered portion being spaced from the opening by a distance equal to between about 0.05 times and about 0.20 times a combined uncompressed thickness of said plurality of absorbent articles.

24. A package comprising a plurality of absorbent articles and reclosable packaging including:

a flexible pocket having a hollow interior sized and shaped for receiving said plurality of absorbent articles;

an opening extending into the hollow interior of the pocket sized and shaped for permitting at least one of said plurality of articles to be withdrawn from the hollow interior of the pocket through the opening; and a flap attached to the pocket adapted for covering the opening to retain said plurality of absorbent articles in the hollow interior of the pocket, said flap being selectably moveable between an open position in which the opening is generally unobstructed by said flap to permit said at least one article to be withdrawn through the opening and a closed position in which the flap covers the opening and an exterior area of the pocket to retain said plurality of articles in the pocket and to prevent said at least one article from passing through the opening, wherein the flap may be rotated when in the closed position about an axis extending normal to a surface of the flap by as much as about twenty degrees without extending past a side of the pocket;

a flexible hinge attached to the pocket adjacent the opening, said flap being attached to the hinge, said hinge having a width substantially equal to a width of the opening and a length equal to between about 0.05 times and about 0.20 times a combined uncompressed thickness of said plurality of absorbent articles.

* * * * *

UNITED STATES PATENT AND TRADEMARK OFFICE
CERTIFICATE OF CORRECTION

PATENT NO.     : 6,601,706 B2
DATED          : August 5, 2003
INVENTOR(S)    : McManus et al.

It is certified that error appears in the above-identified patent and that said Letters Patent is hereby corrected as shown below:

Column 7,
Lines 31 and 34, "shared" should read -- shaped --.
Line 35, "of to" should read -- of absorbent articles to --.

Column 8,
Line 3, "0.052" should read -- 0.058 --.
Line 13, "flip" should read -- flap --.
Line 37, "emit" should read -- permit --.
Line 46, "flag" should read -- flap --.

Column 10,
Line 27, "; and" should read -- ; --.
Line 41, ";" should read -- ; and --.

Column 11,
Line 17, "; and" should read -- ; --.

Column 12,
Line 11, ";" should read -- ; and --.

Signed and Sealed this

Sixteenth Day of March, 2004

JON W. DUDAS
*Acting Director of the United States Patent and Trademark Office*